(12) United States Patent
Vasudevan et al.

(10) Patent No.: US 7,889,840 B2
(45) Date of Patent: Feb. 15, 2011

(54) SYSTEM AND METHOD FOR PREDICTING MATERIAL FATIGUE AND DAMAGE

(75) Inventors: Asuri K. Vasudevan, Reston, VA (US); Kuntimaddi Sadananda, Springfield, VA (US); Grzegorz Glinka, Petersburg (CA); Daniel Kujawski, Portage, MI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 251 days.

(21) Appl. No.: 11/972,146

(22) Filed: Jan. 10, 2008

(65) Prior Publication Data
US 2008/0177516 A1 Jul. 24, 2008

Related U.S. Application Data

(60) Provisional application No. 60/884,316, filed on Jan. 10, 2007.

(51) Int. Cl.
*G01N 23/02* (2006.01)
(52) U.S. Cl. .............................. 378/58; 378/70; 378/210
(58) Field of Classification Search ................... 378/58, 378/70, 210; 703/2
See application file for complete search history.

(56) References Cited

U.S. PATENT DOCUMENTS 6,813,749 B2  11/2004  Rassaian
7,219,044 B1   5/2007  Prevey et al.
2004/0148143 A1  7/2004  Deobald et al.

OTHER PUBLICATIONS

D. Kujawski, "A new ( K*Kmax)0.5 driving force parameter for aluminum alloys", International Journal of Fatigue, V. 23, p. 733-740, 2001.
M. Croft et al., "Strain profiling of fatigue crack overload effects using energy dispersive X-ray diffraction", Int. J. Fatigue, V 27, p. 1408, 2005.
A.H. Norrozi et al., "A two parameter driving force for fatigue crack growth", Int. J. Fatigue, V 27, p. 1277-1296, 2005.
A.K. Vasudevan, K. Sadananda; "Analysis of fatigue crack growth under compression-compression loading" International Journal of Fatigue, V 23 (Supp 1), p. S365-S374, 2001.
K. Sadananda, A.K, Vasudevan, "Short crack growth and internal stresses", Int. J. Fatigue, V. 19 Supp 1, p. S99-S108, 1997.
A.K. Vasudevan, K. Sadananda, N. Louat; A Review of Crack Closure, Fatigue Crack Threshold and Related Phenomena; Materials Science and Engineering A, vol. 188, p. 1-22, 1994. Also published as NRL report R-1994-37265, 1994.

(Continued)

*Primary Examiner*—Jurie Yun
(74) *Attorney, Agent, or Firm*—Amy Ressing; Sally A. Ferrett

(57) ABSTRACT

A method and system for determining damage prediction of a component. The component may be critical component used in an aircraft or other vehicle experiencing cyclic loading. The method and system determines the $\Delta K$, $K_{max}$ and $K_{internal}$ values for the component and utilizes these values in order to predict damage and/or failure of the component.

15 Claims, 19 Drawing Sheets

OTHER PUBLICATIONS

K. Sadananda, A.K. Vasudevan; "Nonpropagating incipient cracks from sharp notches under fatigue", Acta Materialia, V 52 (14), p. 4239-4249, 2004.

K. Sadananda, A.K. Vasudevan, I.W. Kang; "Effect of superimposed monotonic fracture modes on the K and Kmax parameters of fatigue crack propagation", Acta Materialia, v 51 (12), p. 3399-3414, 2003.

A.K. Vasudevan, K. Sadananda, R.L. Holtz; "Analysis of vacuum fatigue crack growth results and its implications" International Journal of Fatigue, V 27, p. 1519-1529, 2005.

K. Sadananda, A.K. Vasudevan, N. Phan; "Analysis of endurance limits under very high cycle fatigue using a unified damage approach"; International Journal of Fatigue, v 29 (9-11), p. 2060-2071, 2007.

A.K. Vasudevan, K. Sadananda; "Transient stress effects on fatigue crack growth thresholds due to testing methodology"; International Journal of Fatigue, V 29 (9-11), p. 1985-1989, 2007.

K. Sadananda, A.K. Vasudevan; "Fatigue crack growth behavior of titanium alloys"; International Journal of Fatigue, V 27 (10-12), p. 1255-1266, 2005.

E.U. Lee, A.K. Vasudevan, K. Sadananda; "Effects of various environments on fatigue crack growth in Laser formed and IM Ti-6Al-4V alloys"; International Journal of Fatigue, V 27 (10-12), p. 1597-1607, 2005.

K. Sadananda, A.K. Vasudevan; "Fatigue crack growth mechanisms in steels"; International Journal of Fatigue, V 25 (9-11), p. 899-914, 2003.

T.S. Srivatsan, Meslet Al-Hajri, V.K. Vasudevan; "Cyclic plastic strain response and fracture behavior of 2009 aluminum alloy metal-matrix composite"; International Journal of Fatigue, V 27 (4), p. 357-371, 2005.

A.K. Vasudevan, K. Sadananda, G. Glinka; "Critical parameters for fatigue damage"; International Journal of Fatigue, V 23 (Supplement1), p. S39-S53, 2001.

K. Sadananda, A.K. Vasudevan; "Analysis of fatigue crack growth behavior in polymers using the unified approach"; Materials Science & Engineering. A: Structural Materials: Properties, Microstructure and Processing, Issue 387-389, pp. 536-541, 2004.

K. Sadananda, A.K. Vasudevan, R.L. Holtz; "Extension of the Unified Approach to fatigue crack growth to environmental interactions"; International Journal of Fatigue, V 23 (Supplement1), p. S277-286, 2001.

U.B. Halabe, A Vasudevan, H.V.S. GangaRao, et al.; "Nondestructive evaluation of fiber reinforced polymer bridge decks using digital infrared imaging", Southeastern Symposium on System Theory, p. 372-275, 2003.

T.S. Srivatsan, Meslet Al-Hajri, W. Hannon, et al.; "The strain amplitude-controlled cyclic fatigue, defomation and fracture behavior of 7034 aluminum alloy reinforced with silicon carbide particulates"; Materials Science & Engineering. A: Structural Materials: Properties, Microstructure and Processing, V 379 (1-2), p. 181-196, 2004.

B. Holper, H. Mayer, A.K. Vasudevan,et al.; "Near threshold fatigue crack growth in aluminium alloys at low and ultrasonic frequency: Influences of specimen thickness, strain rate, slip behaviour and air humidity" International Journal of Fatigue, V 25 (5), p. 397-411, 2003.

B. Holper, H. Mayer, A.K. Vasudevan, et al.; "Near threshold fatigue crack growth at positive load ratio in aluminium alloys at low and ultrasonic frequency: influences of strain rate, slip behaviour and air humidity"; International Journal of Fatigue, V 26 (1), p. 27-38, 2004.

K. Sadananda, A.K. Vasudevan; "Crack tip driving forces and crack growth representation under fatigue", International Journal of Fatigue, V 26 (1), p. 39-47, 2004.

Xuejun Fan, G., Rasier, V.S., Vasudevan, A.K.; "Effects of Dwell Time and Ramp Rate on Lead?Free Solder Joints in FCBGA Packages"; Electronic Components and Technology Conference, IEEE 1441379, p. 901-906, 2005.

T.S. Srivatsan, S. Anand, S. Sriram, et al.; "The high-cycle fatigue and fracture behavior of aluminum alloy 7055", Materials Science & Engineering. A, V 281 (1-2), p. 292-304, 2000.

V. Vasudevan, X.Fan, T. Liu, et al.; "Slow Cycle Fatigue Creep Performance of Pb-Free (LF) Solders", Electronic Components and Technology Conference, IEEE 4249871, 2007.

R.V. Uppalapati, K. Leiser, M.Sickle, et al.; "Board Design Influence on BGA Mechanical Reliability", Electronic Components and Technology Conference, IEEE 4250125, p. 1788-1795, 2007.

A.K. Vasudevan, K. Sadananda, "Classification of Fatigue Crack Growth Behavior", Metallurgical and Materials Transactions A—Physical Metallurgy and Materials Science, V. 26 (5), p. 1221-1234, 1995. Also printed as NRL Report R-1995-38360, 1995.

A.H. Norrozi et al., "A two parameter driving force for fatigue crack growth", Int. J. Fatigue, V 27, p. 1277-1296, 2005.

Paris, P.C., Gomez, M.P., and Anderson, W.E., "A Rational Analytic Theory of Fatigue", The Trend in Engineering, vol. 13, pp. 9-13, (1961).

INPUT: $K_{max,tot} = K_{max,appl} - K_r$ AND $\Delta K_{tot} = \Delta K_{appl} - K_r$ $$\frac{1}{E}\left(\frac{K_{max,tot} \times \psi_{y,1}}{\sqrt{2\pi\rho^*}}\right)^2 = \frac{(\sigma^a_{max})^2}{E} + \sigma^a_{max}\left(\frac{\sigma^a_{max}}{K'}\right)^{\frac{1}{n}}$$

$$\varepsilon^a_{max} = \frac{\sigma^a_{max}}{E} + \left(\frac{\sigma^a_{max}}{K'}\right)^{\frac{1}{n}}$$

$$\frac{1}{E}\left(\frac{\Delta K_{tot} \times \psi_{y,1}}{\sqrt{2\pi\rho^*}}\right)^2 = \frac{(\Delta\sigma^a)^2}{E} + 2(\Delta\sigma^a)\left(\frac{\Delta\sigma^a}{2K'}\right)^{\frac{1}{n}}$$

$$\frac{\Delta\varepsilon^a}{2} = \frac{\Delta\sigma^a}{2E} + \left(\frac{\Delta\sigma^a}{2K'}\right)^{\frac{1}{n}}$$

$\sigma^a_{max} \longrightarrow \sigma^a_{max} \frac{\Delta\varepsilon^a}{2} \Leftarrow SWT \longleftarrow \Delta\sigma^a$ $$\frac{(\sigma'_f)^2}{E}(2N_f)^{2b} + \sigma'_f \varepsilon'_f (2N_f)^{b+c} = \sigma^a_{max} \frac{\Delta\varepsilon^a}{2} \longrightarrow N_f \longrightarrow \boxed{\frac{da}{dN} = \frac{\rho^*}{N_f}}$$

FIG. 6

SYSTEM AND METHOD FOR PREDICTING MATERIAL FATIGUE AND DAMAGE

CROSS-REFERENCE TO RELATED APPLICATIONS

This Application is a non-provisional application of provisional (35 USC 119(e)) application 60/884,316 filed on Jan. 10, 2007, the entire disclosure of which is incorporated herein in its entirety.

BACKGROUND

1. Field of the Invention

The field of the invention is related to methods and systems for predicting material fatigue and damage. In particular the invention relates to an improved method and system for applying an improved model of material fatigue and damage for a component design, maintenance and its life prediction.

2. Description of the Related Technology

The construction and maintenance of aircraft is a complex undertaking that can result in catastrophic effects if performed improperly. During the manufacture and usage of structural components of aircraft various defects can occur. Defects can occur during the manufacture and fabrication of components. Defects can also occur during the assembly, repair and maintenance of the structural components. These defects may be latent in the structural material used in the construction of a component and may therefore exist well before actual fabrication of the component. Pre-existing defects can result in cracks being initiated under a variety of service loading and environmental conditions. Such defects can occur well below the non-destructive (NDE) inspection limits, and grow with service, finally leading to failure of the components.

Depending on the function and usage of aircraft components, the failure impact on the overall system can vary from a minor degradation to catastrophic failure. Histories of aircraft failures have indicated that failure causes are mostly initiated due to: (1) stress concentration sites such as such as rivet holes, lap joints, wing root areas etc.; (2) defects introduced during inspection, repair and assembly; or (3) initial manufacturing defects. These causal relationships have had a major effect on: (1) design philosophy, (2) the selection and use of materials with low incidences of defects, and (3) the introduction of FAA enforced periodic inspection and maintenance procedures.

Over the past four decades, there have been about 70 different crack initiation and about 40 crack growth empirical models proposed. Since the early 1970's, these models have been presented in terms of computer algorithms for predicting the life of components. There are several computer models that have been proposed by engineers in various countries to predict the life of a component using service load data. These models have not succeeded in making consistently reliable predictions. A few examples of these models are: CORPUS (from Greece), PREFAS (from Portugal), ONERA (from France), MODGRO (from US Air Force) and FASTRAN (from US NASA). FASTRAN is sometime labeled as NASTRAN.

In FIG. 1, the life predictions from the above mentioned models for an aircraft spectrum under a flight-by-flight load history for 2024 alloy (using as a mean load of 75 MPa) are compared. All of these models tend to under predict the flights to failure, with the FASTRAN model most closely approximating the test data. The models can also over predict the flights to failure. Additional details regarding FIG. 1 can be found in Lazzeri L, Pieracci A, Salvetti A; 18th Symposium of International Committee on Aeronautical Fatigue, Melbourne (Australia), May 1995.

Commonly, the inadequacies of the predictive abilities of the models are compensated by using several adjustable parameters which are correlated and tuned using lab test data. Due to the uncertainty in predictive capabilities, vehicle safety is guarded using a variety of methods. These methods may involve the use of safety factors in design, the selected use of component data, conducting periodic non-destructive (NDE) inspections, the use of statistics to assign data scatter and institution of material quality control procedures.

Ultimately the drawbacks in the current fatigue life prediction methods stem from several sources: (1) the assumption of plasticity induced crack closure; (2) the lack of terms in the models that relate to the environmental effects and slip deformation behavior of materials; (3) the requirement of several adjustable parameters that are needed in order to fit the observed data; and (4) the need for extensive lab test data to determine the adjustable parameters. Furthermore, past models use only one driving force parameter, $\Delta K$, which is based on the "crack closure" model. Such models are not applicable to different types of service load-history and they are not applicable to all types of materials and platforms. They also cannot reliably predict component response to compression dominated service loads or predict crack initiation. Due to these drawbacks, the lack of reliability and predictability of past models stem from inaccurate and inadequate accounting of fatigue damage forcing them to be mere curve-fitting models.

Additional aspects of the invention will be apparent from the following summary, drawing figures, and detailed description.

BRIEF SUMMARY OF THE INVENTION

An object of the present invention may be the provision of a method for predicting damage to a component.

Another object of the present invention may be the provision of a system for predicting damage to a component.

An aspect of the invention may be a method for component damage prediction comprising: determining $\Delta K_{applied}$ (hereinafter "$\Delta K_{appl}$") of the component; determining $K_{max,appl}$ of the component; determining $K_{internal}$ (hereinafter "$\Delta K_{int}$") of the component; wherein the $\Delta K_{appl}$ and the $K_{int}$ of the component are used to determine $\Delta K_{total}$ of the component; and using the $K_{max,total}$, the $K_{int}$ and the $\Delta K_{total}$ of the component to predict damage to the component.

Another aspect of the invention may be the provision of a system for component damage prediction comprising: a sensor enabled to determine empirical data related to the component; a receiver operably connected to a computer; a database operably connected to the computer, wherein material data related to the component is stored; wherein the computer is programmed to use the empirical data and the material data related to the component in order to predict damage, and wherein the experimental data and the material data are used to determine $\Delta K_{appl}$, $K_{max,appl}$ and $K_{int}$ of the component.

Yet another aspect of the invention may be the provision of a method for component damage prediction comprising: determining $\Delta K_{appl}$ of the component; determining $K_{max,appl}$ of the component; determining $K_{int}$ of the component, wherein the step of determining $K_{int}$ is performed using a non-destructive method; wherein at least one of the steps of determining the $\Delta K_{appl}$, the $K_{max,appl}$ and the $K_{int}$ is performed using a sensor; and using the $K_{max,total}$ the $K_{int}$ and the $\Delta K_{total}$ to predict damage to the component, wherein the step of using the $K_{max,total}$ the $K_{int}$ and the $\Delta K_{total}$ of the component to predict damage to the component comprises utilizing the relationship $(da/dN)=C\{\Delta K^{1-p}_{total}K^{p}_{max,total}\}^{\gamma}$ or a lookup table in terms of $\Delta K_{total}$ and $K_{max,total}$.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 6 is shows the calculation of the fatigue crack growth from the crack tip strain life data.

DETAILED DESCRIPTION OF THE INVENTION

The invention is directed to a system and method for predicting component damage. In order to create a more reliable life prediction model for components, the basic physics of the problem are analyzed and a better approach is formulated in order to treat the overall damage as an intrinsic behavior of the material. This is accomplished by recognizing that: (1) the true material behavior is represented by the long crack growth properties, (2) fatigue damage must be described by two parameters, $\Delta K_{appl}$ and $K_{max,total}$ instead of merely one (i.e. $\Delta K$), and (3) the deviations from the long crack growth behavior arise from the internal stresses present ahead of the crack tip which contribute predominantly to $K_{max}$. These internal stresses are either present in the material or generated ahead of the crack tip during overloads and underloads. The internal stresses can be tensile or compressive and are responsible for an accelerated growth in the short crack region, and decelerated growth while those generated by overloads tend to decelerate crack growth. In general, the overall fatigue damage must be described from the initiation stage to the final failure. This assists in the determination of potential failure for components.

Throughout the application the term "component" is typically used in reference to aircraft components, however it should be understood that the inventive method and system may be applied to other vehicles and structures in addition to aircraft (e.g. ships, buildings, bridges, cars, etc.). Discussions referring to aircraft components are by way of example only and are not meant to limit the application of the method and system. Additionally, the term "component" should be understood to mean any part of the vehicle or structure that contributes to the overall vehicle or structure (e.g. strut, beam, wing part, etc.).

Figure 1:
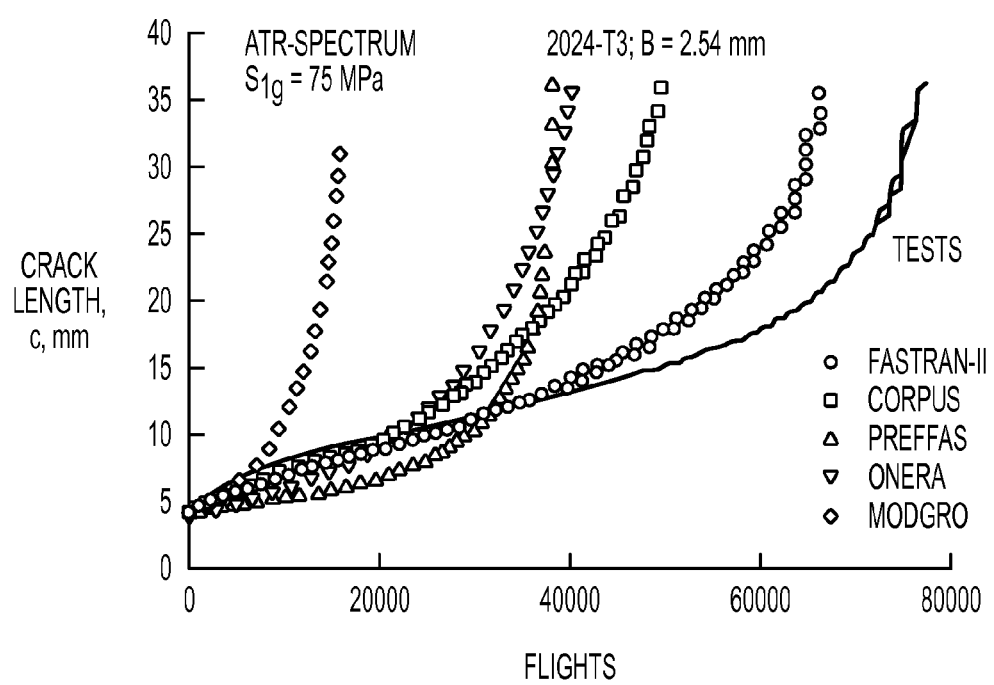
FIG. 1 is a graph of life expectancy in terms of flights predicted by existing predictive algorithms.
Figure 2:
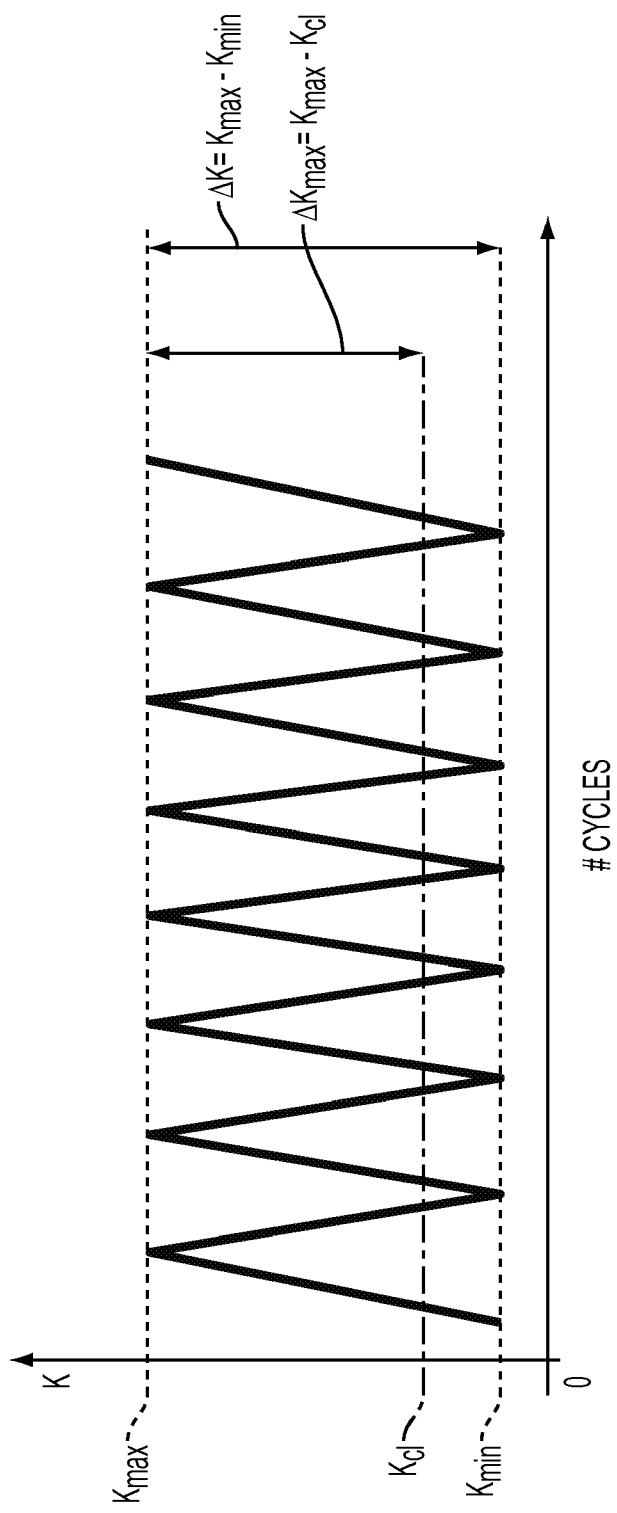
FIG. 2 is a graph showing the stress intensity factors of a crack cyclically loaded between $K_{max}$ and $K_{min}$.

For long cracks, defined as the crack length being larger than the plastic zone at the crack tip, there is a threshold stress intensity $\Delta K_{th}$ (defined at crack growth rates $10^{-10}$ m/cycle by ASTM-E64 standards) below which cracks do not propagate. The threshold values for a given material have been experimentally observed to depend on the stress ratio $R=K_{max}/K_{min}$, the microstructure of the material (e.g. grain size, precipitates, dispersed particles, etc.) and the testing environment (e.g. lab air, NaCl, temperature, etc). The stress ratio R effects on $\Delta K_{th}$ have been rationalized on the basis of a premature crack closure in the wake of a crack that reduces the applied stress intensity $\Delta K_{appl}=K_{max}-K_{min}$ by an amount due to the closed crack, $K_{closure}$. Therefore, the 'effective' driving force $\Delta K_{effective}=K_{max}-K_{closure}$ can be less than the applied force $\Delta K_{appl}$, which results in "retarding" the crack growth process. FIG. 2 schematically describes various stress intensity factors of a crack cyclic loaded between $K_{max}$ and $K_{min}$. FIG. 2 also provides the definitions of the loading parameters $\Delta K_{effective}$, $K_{max}$ and $\Delta K_{appl}$ with and without crack closure.

The effect of crack closure is that it retards the crack growth process. The sources for this crack closure may be attributed to: (1) plasticity, (2) asperities from oxides or corrosion products, (3) surface roughness, (4) viscous fluids, and (5) phase transformed material that lies ahead of the crack tip.

Figure 3:
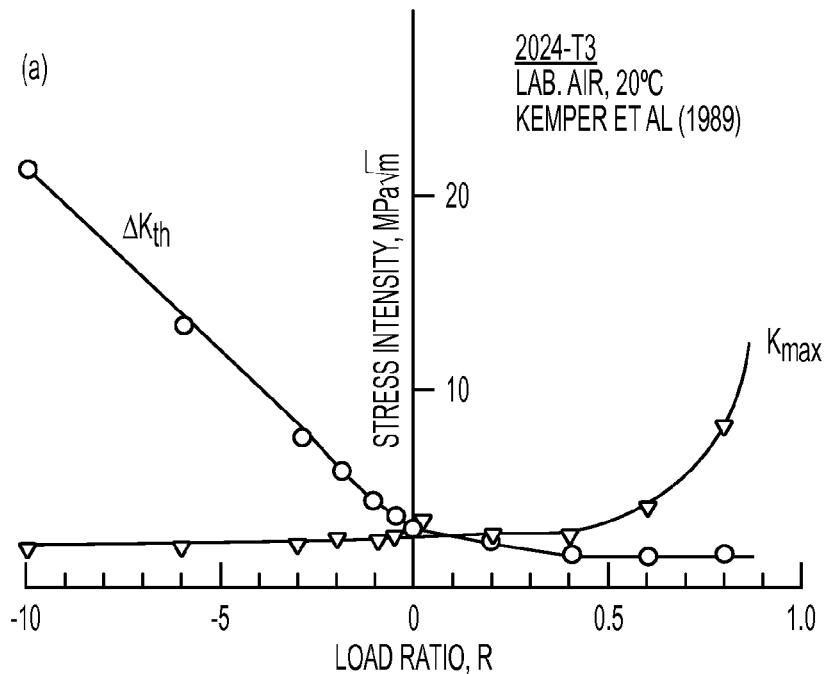
FIG. 3 is a graph of the threshold values of both $\Delta K_{threshold}$ (hereinafter "$\Delta Kh$") and $K_{max}$ plotted against the stress ratio R.

This concept can be illustrated by using an example from the behavior of 2024-T3 aircraft alloy that is used in the lower wings of aircraft. This alloy is chosen due to the availability of large amount of data from Kemper's thesis taken over a very wide range of stress ratios. FIG. 3 shows the threshold values of both $\Delta K_{th}$ and $K_{max}$ conventionally plotted against the stress ratio R from −10 to +0.8. The data shows that $\Delta K_{th}$ decreases linearly with R until R=0.4, and then levels off. $K_{max}$ decreases to level as R is decreased and is constant in the R range when $\Delta K$ is decreasing. A critical stress intensity $\Delta K^*_{th}$ has been designated when R>0.4. In the region where R>0.4, $K_{max}$ increases non-proportionately while $\Delta K_{th}$ remains constant. This portion of the plot is labeled as a $\Delta K$-controlled region, where $K_{max}$ must increase to maintain constant $\Delta K_{th}$ for crack growth. As R→1, $K_{max}$ increases to a high level dictated by other failure mechanisms such as overload or static load fracture. On the other hand, in the region where R<0.4, $K_{max}$ approaches a constant critical value $K^*_{max}$ with a corresponding increase in $\Delta K_{th}$. This portion of the plot is labeled as the $K_{max}$ controlled region, which means that $\Delta K_{th}$ must be varied to maintain the critical $K^*_{max}$ constant for crack growth. In the entire range of R=−10 to 0.8, while both critical values of and $\Delta K^*_{th}$ and $K^*_{max}$ are being satisfied, either one or the other parameter may be controlling the overall fatigue damage process. Thus, the crack extension will occur only if these two critical stress intensities, $\Delta K^*_{th}$ and $K^*_{max}$ are simultaneously exceeded. These two limiting values are the minimum conditions necessary for crack growth to occur, independent of any closure mechanisms present. The magnitudes of these two critical stress intensities can vary for a given alloy and depend on the load history and environmental conditions.

Figure 4:
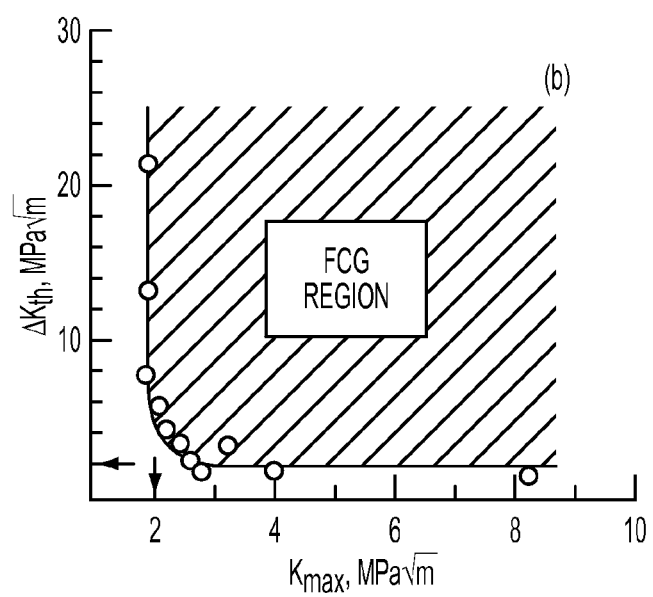
FIG. 4 is a graph of $\Delta K_{th}$ and $K_{max}$ plotted against each other.

Because R is not a driving force for crack growth, the data from FIG. 3 can be re-plotted in terms of $\Delta K_{th}$ and $K_{max}$. The result, shown in FIG. 4, is an L-shaped curve that defines the region where crack growth is permissible. The critical values of $\Delta K^*_{th}$ and $K^*_{max}$ are shown by the arrows along the axes of the plot. For the 2024 alloy, the two critical values of $\Delta K^*_{th}$ and $K^*_{max}$ are about 1.8 and 2.1 MPa√m, respectively. Such interpretations are independent of testing methods and are applicable to a variety of materials. In addition, the methodology is applicable not only for the threshold region, but for all crack growth rates.

Trends in the experimental fatigue results of various types of materials are the following physical bases for crack growth. The two driving force parameters $\Delta K$ and $K_{max}$ are intrinsic to the material behavior and are needed to uniquely define the cyclic damage, independent of crack closure. The critical thresholds $\Delta K^*_{th}$ and $K^*_{max}$ are material parameters and depend on the alloy chemistry, microstructure, deformation slip mode and environment. The two critical parameters are also independent of testing methods. The longer crack growth behavior represents a material behavior for a given environment.

Figure 5:
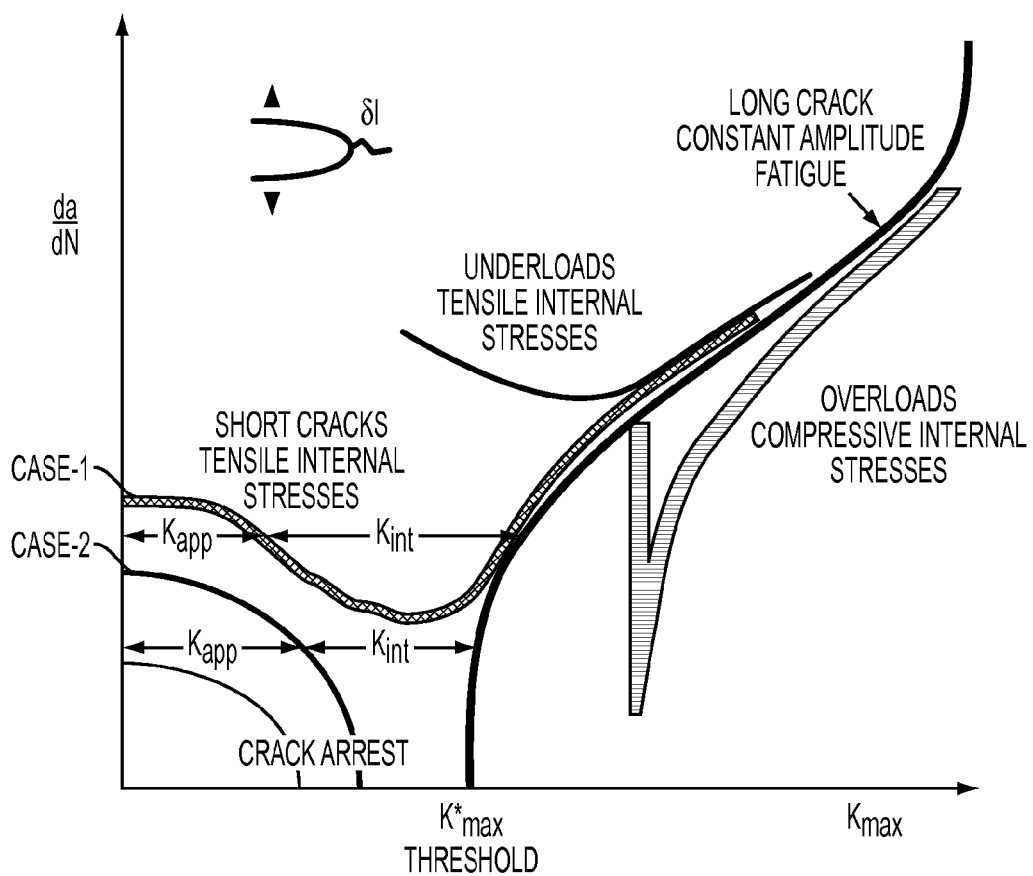
FIG. 5 is a graph illustrating the deviations from the long crack behavior due to tensile and compressive stress from short cracks, under-loads and overloads.

It is experimentally observed that there are departures from long crack growth behavior which are noticed in the short crack (defined as crack length shorter than its plastic zone size) growth region where cracks can grow faster below the long crack thresholds. Sometimes after underloads cracks can accelerate and after overloads cracks can decelerate. These deviations can occur below and above the long crack threshold values ($\Delta K^*_{th}$ and $K^*_{max}$). Such observations are due to internal stresses generated under specific conditions of loading. The internal stresses can be tensile in nature, as in short cracks and underloads, resulting in crack acceleration; while in the case of overloads these can be compressive stresses that will retard the crack growth. Thus the internal stress bridges the gap between the two regions and provides unified crack growth behavior, which results in the unified fatigue damage approach. Using the long crack growth property as the fundamental behavior, one can now connect the entire range of damage from the short crack (which is at the nucleation stage) and the long crack (which is at the NDE inspection range and above) and final failure. FIG. 5 shows the deviations from the long crack behavior due to tensile and compressive stress from short cracks, underloads and overloads. Internal stress correction to short cracks is in addition to any other corrections needed in the computation of stress intensity factor K, due to shortness of the crack. Internal stress contribution is considered as a dominant factor for most of the short crack growth.

Figure 19:
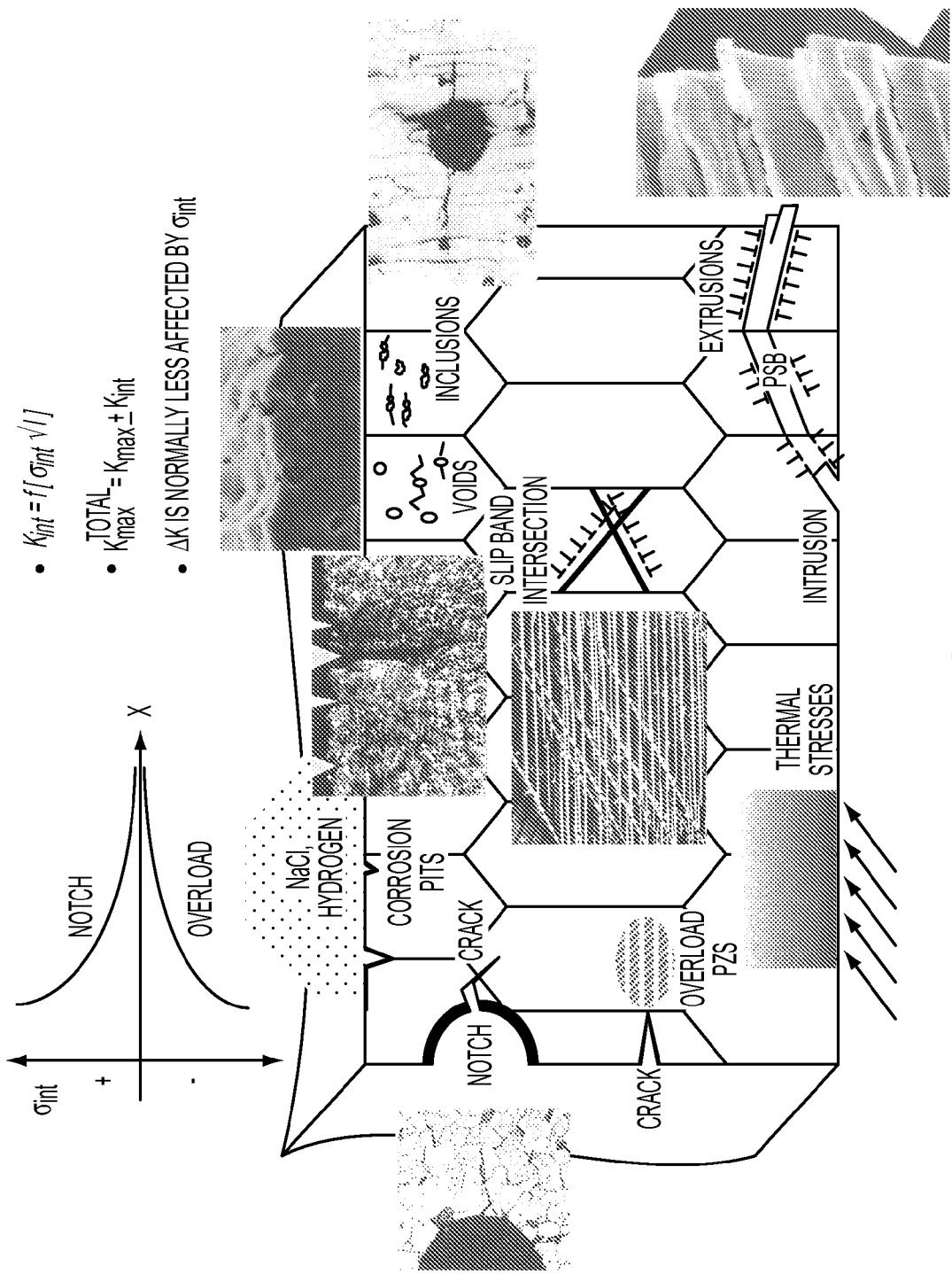
FIG. 19 illustrates some examples of internal stresses that can affect fatigue life.

FIG. 19 illustrates examples of sources of internal stresses that affect fatigue life, including notches, cracks, thermal stresses, intrusions, slip band intersections, voids, inclusions, NaCl and hydrogen environments, corrosion pits, extrusions, and PSBs.

Internal stresses can arise from several sources such as: notch tip stresses, crack tip stresses, microvoids and inclusions, thermal stresses, residual stresses from cold work, shot-peening, machining etc., contributions from corrosion and from temperature. The term internal stress encompasses all of these aforementioned types of stresses. A correct assessment of crack tip forces must then include all of the stresses applicable to the situation, both the applied and internal. All these are stresses that affect the crack growth behavior and these stresses have to be quantified correctly to account for their overall contribution to the damage. Within the assumptions of linear elasticity, the internal stresses are additive to the applied stress. The total driving force for any crack to grow requires the criterion:

$$\Delta K_{total} \pm \Delta K_{appl} \pm \Delta K_{internal} > \Delta K^*_{th}, \text{ threshold for a long crack.} \quad (1)$$

$$K_{max,total} \pm K_{max,appl} \pm K_{max,internal} > K^*_{max}, \text{ threshold for a long crack.} \quad (2)$$

The parameters $\Delta K_{int}$ and $K_{max,internal}$ pertain to the contributions from "internal stresses" from residual stresses, corrosion or temperature. The sign can be positive or negative depending on the tensile or compressive internal stresses. The time dependent contributions to internal stress can also come from phenomena such as corrosion, oxidation or deformation such as creep and monotonic loads where mechanisms of deformation can change with time. Equations (1) and (2) suggest that for a given constant-amplitude loading and environment, the long crack growth is a fundamental property of the material represented by the intrinsic threshold values $\Delta K^*_{th}$ and $K^*_{max}$ of the material. When any deviation (positive or negative) from the long crack behavior is observed, the additional contributions from the internal stresses should be included with the applied driving forces $\Delta K_{appl}$ and $K_{max,appl}$ in estimating the total crack tip driving force. Thus, the entire fatigue damage is described by two parameters that determine total crack tip driving force, $\Delta K_{appl}$ and $K_{max,appl}$ instead of just one parameter $\Delta K$ that is commonly used in all the earlier models. This is incorporated into the following equation.

$$(da/dN) = f(\Delta K, K_{max}, K_{int}) \quad (3)$$

The above relationship establishes the basic physics of the damage. Using the relationship shown in equation 3 as a guideline, a physics-based unified fatigue damage model is used that takes into account the crack initiation stage to final failure while having no adjustable parameters. Since the model is physics based, the damage is described ahead of the crack-tip as opposed to the crack closure concepts that are operative behind the crack-tip. The model is applicable to all materials, service loads, and platforms. Also, the model is able to predict long time service loads. This model is called the UNIGROW Model, which is represent in a generic form below:

$$\frac{da}{dN} = C\{\Delta K_{total}^{1-p} K_{max,total}^{p}\}^{\gamma} \quad (4)$$

The exponents 'p' and 'γ' are obtained from derivations of the strain-controlled (Coffin-Manson $\Delta\epsilon$–$N_f$ curve) fatigue experiments. 'p' is related to the plastic and elastic slopes of strain controlled fatigue data. 'γ' is related to the cyclic work hardening rate. The above mentioned equation is derived by combining the Neuber equation with the Ramburg-Osgood relation and the Smith-Watson-Topper (SWT) parameter. The constant 'C' is computed from both a Coffin-Manson curve and fatigue crack growth data obtained from lab coupon samples.

The method involves relating the far-field loads to the crack tip stress-strain behavior in a quantitative manner in a small element of dimension ρ*. The small element of dimension ρ* is imbedded in the parameter 'C.'. The crack is allowed to grow incrementally by an amount ρ*, while keeping track of the local stress-strain variations during every cycle of growth. The 'internal stress' contributions are first mapped experimentally using controlled experiments involving overloads and then measuring the crack tip displacements using Synchrotron XRD (X-ray diffraction method)) as a function of distance away from the crack tip. It is possible to use other non-invasive methods besides X-ray diffraction in order to obtain the desired results.

This experimental observation is then estimated analytically using mechanics principles to obtain the results of internal stress variation with crack length. The result is then incorporated into the final equation in order to predict the life of the component. The final life is represented in terms of crack length 'a' vs. number of cycles 'N', which is accomplished by integrating equation (4) with respect to the crack length. The chart shown in FIG. 6 gives a summary of the procedure to equation (4). FIG. 6 shows the calculation of the fatigue crack growth from the crack tip stain-life data.

In order to calculate $K_{int}$ the internal stresses, $\sigma_{int}$, (or the residual stresses, $\sigma_{res}$,) have to be determined. $\sigma_{int}$ is defined as the stresses normal to the crack plane at the minimum applied load, $P_{min}$. When the applied load $P_{min}=0$, the corresponding internal stresses are called the residual stresses, $\sigma_{res}$. Discussed below are various methods for calculating $K_{int}$.

The modified Rice equation is used in the plastic zone and the linear-elastic solution is used outside of the plastic zone. The elastic solution is offset in the direction of crack propagation by the amount needed to coincide with the yield point from the Rice equation (approximately half of the plastic zone size). For a given x, the $\sigma_{int}$ is determined as:

$$\sigma_{int} = \sigma_{min} = \sigma_{max} - \Delta\sigma \quad (5)$$

The values for $\sigma_{max}$ using the Rice equation and the Elastic equation are shown below.

$$(\text{Rice}) \sigma_{max} = \sigma_0 \left( \frac{K_{max}}{(1+n')\pi\sigma_0^2(x+\rho^*)} \right)^{n'/1+n'} \quad (6)$$

$$(\text{Elastic}) \sigma_{max} = \frac{K_{max}}{(2\pi(x+\rho^*))^{1/2}} \quad (7)$$

The values for $\Delta\sigma$ using the Rice equation and the Elastic equation are shown below:

$$(\text{Rice}) \Delta\sigma = 2\sigma_0 \left( \frac{\Delta K}{4(1+n')\pi\sigma_0^2(x+\rho^*)} \right)^{\frac{n'}{1+n'}} \quad (8)$$

$$(\text{Elastic}) \Delta\sigma = \frac{\Delta K}{(2\pi(x+\rho^*))^{1/2}} \quad (9)$$

In equations 6 through 9, 'x' is the distance from the crack tip, ρ* is the process zone size, n' is the cyclic strain hardening exponent, and $\sigma_0$ is the yield strength. The size of the process zone, ρ*, can be determined from the condition that the strain in the process zone cannot be larger than the ultimate strain of the material.

Instead of using the modified Rice equations 6-9 above, the HRR (Hutchinson, Rice and Rosengreen) equations can be used. Additionally, the Paris-Creager solution for a blunt crack can be used to calculate the elastic stress distribution. Then, using the Neuber rule, the elastic-plastic internal stresses can be estimated. Alternatively, the internal stresses can be computed using an appropriate elastic-plastic FEA software package.

The internal stress intensity factor, $K_{int}$, or $K_{res}$, can be calculated using one of the following methods: (1) it be calculated analytically by using the weight function or clamping force method; (2) it can be done numerically by calculating the internal stresses, $\sigma_{int}$, for a known geometry and applied loading, or (3) the corresponding internal stress intensity factor $K_{int}$ can be calculated.

The internal stress intensity factor, $K_{int}$ or $K_{res}$, can be determined experimentally using the following relationships:

$$K_{int} = K_{min}^{appl} - K_{PR} \text{ for } K_{min}^{appl} \geq 0 \text{ and} \quad (10)$$

$$K_{int} = -K_{PR} \text{ for } K_{min}^{appl} < 0$$

$K_{PR}$ is the crack re-propagation stress intensity factor. After the $K_{int}$ is determined, the total values of $K_{min}^{appl}$ and $-\Delta K_{total}$ are calculated. The applied values of $K_{max}$ and $\Delta K_{appl}$ can be modified using the internal stress intensity factor $K_{int}$ and the relationships below:

$$K_{max}^{total} = K_{min}^{appl} + K_{int} \text{ and } \Delta K_{total} = \Delta K_{appl} + K_{int}, \quad (11)$$

$$K_{max}^{total} = K_{max}^{appl} + K_{int} \text{ and } \Delta K_{total} = \Delta K_{appl}, \text{ or} \quad (12)$$

$$K_{max}^{total} = K_{max}^{appl} \text{ and } \Delta K_{total} = \Delta K^{appl} + K_{int}. \quad (13)$$

The two parameter crack driver force ΔK is calculated as shown in the equation below.

$$\Delta\kappa = (K_{max}^{total})^p (\Delta K^{total})^{1-p} \quad (14)$$

The relationship between the crack growth rate, da/dN, versus Δκ may be determined graphically, numerically, or analytically. The relationship between da/dN versus Δκ is used for fatigue crack growth prediction. These relationships can be summarized as shown in FIG. 7.

Figure 7:
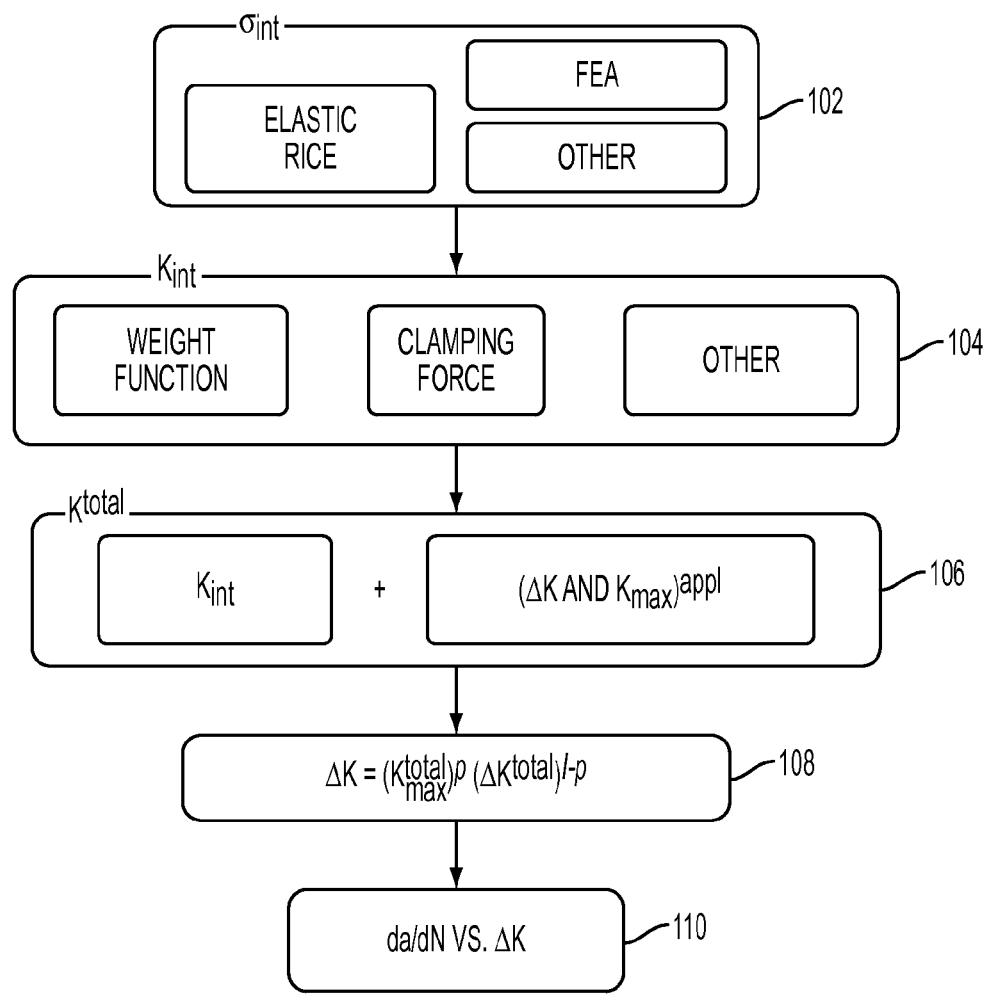
FIG. 7 is a flow chart of the procedure for performing the $K_{int}$ calculation.

Referring to FIG. 7, at step 102, the various methods for calculating $\sigma_{int}$ are shown, generally through the usage of the Elastic or Rice equations, although other equations may be used, should they be applicable. At step 104, the methods used for determining $K_{int}$ are shown, generally by using weight functions, clamping force, or other similar methods. At 106, the method for calculating $K_{total}$ is shown, which involves the addition of $K_{int}$ and $\Delta K_{appl}$ and $K_{max,appl}$. At step 108, Δκ is determined based upon $(\Delta K^{1-p}_{total})(K^p_{max,total})$. At step 110, da/dN versus Δκ can be analyzed.

The residual stresses ahead of the crack tip and subjected to loading are also calculated. This is accomplished using the generalized Neuber or Equivalent Strain Energy Density method. Both methods are based on the hypothesis that the strain energy density in the plastic zone ahead of the crack tip remains the same as it would be in a linear elastic material. Therefore the strain energy density ahead of the crack tip can be determined by using linear elastic solutions available in the literature. The linear elastic strain-stress distribution ahead of a crack tip is used as the input for calculating the actual elastic-plastic strains and stresses in the crack tip plastic zone. Hencky's equations of total deformation plasticity theory may also be used together with the material memory.

The method for calculating the residual stresses applies the generalization of the Neuber rule to arbitrary multi-axial stress states. The original Neuber rule was derived for a uniaxial stress state only. The procedure shown in FIG. 8 applies derivation and validation of appropriate mathematical equations for arbitrary material stress-strain curves. Furthermore, the procedure provides for the development of a model combining the multi-axial Neuber rule, the Hencky equations and the Mroz memory model thereby enabling calculation of elastic-plastic crack tip strains and stresses induced by cyclic loading. Additionally, the procedure can also provide for the development of a numerical solution procedure for calculating the elastic-plastic crack tip strains and stresses for a wide range of material stress-strain constitutive curves and variable amplitude cyclic loading. A set of computer programs are used for processing the input data and calculating the elastic-plastic strains and stresses ahead of a crack tip subjected to cyclic loading.

Figure 8:
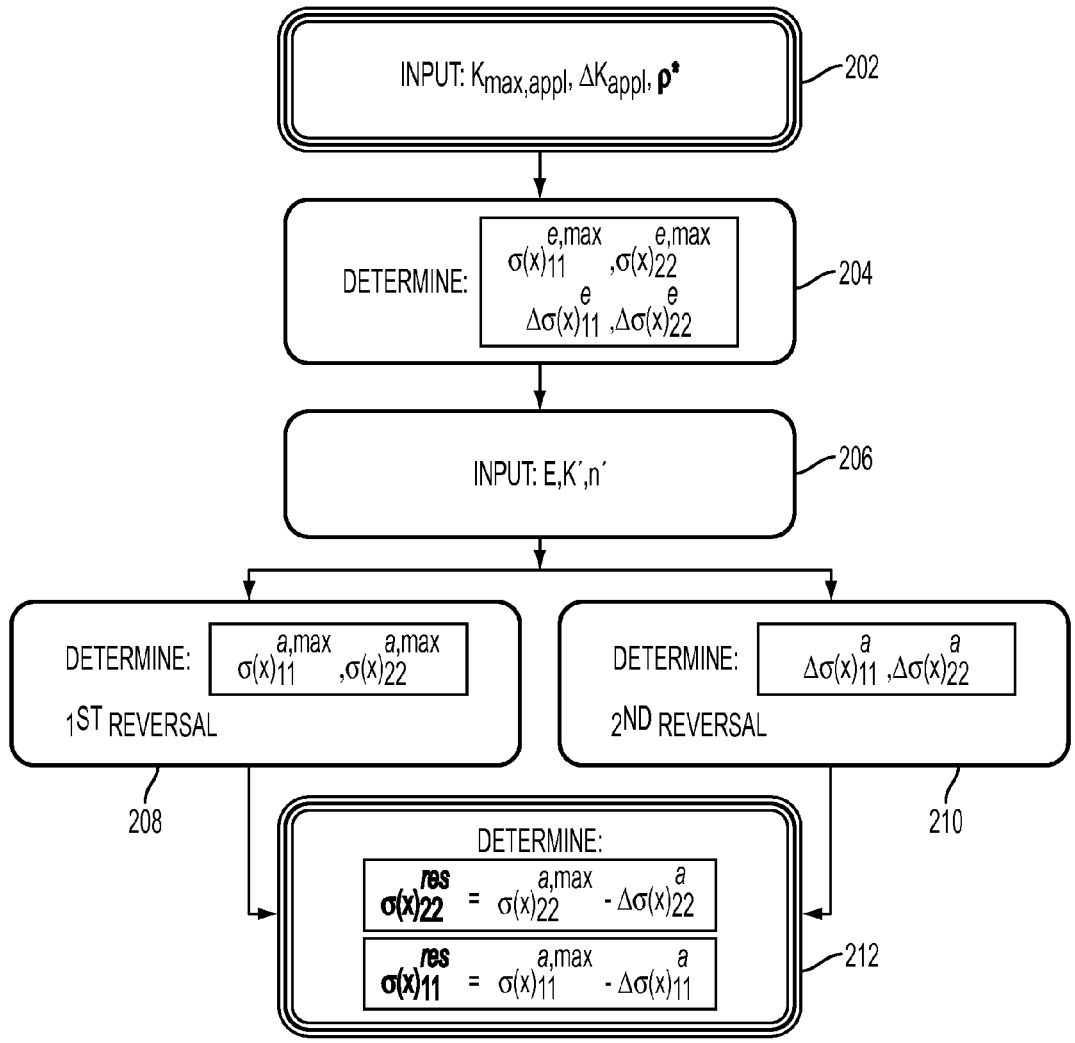
FIG. 8 is a flow chart of the procedure for calculating multi-axial residual stress ahead of a fatigue crack.

In general, the procedure for calculating multi-axial residual stresses ahead of a fatigue crack is shown in FIG. 8. At step 202 the values $K_{max,appl}$ $\Delta K_{appl}$ and p* are input. At step 204 the values for $\sigma(x)_{11}$, $\Delta\sigma(x)_{11}$, $\sigma(X)_{22}$ and $\Delta\sigma(x)_{22}$ are determined. At step 206 the values for E, K' and n' are input. At step 208 the $1^{st}$ reversal is determined. At step 210 the $2^{nd}$ reversal is determined. At step 212 the values previously obtained are used to determine the multi-axial residual stresses ahead of a fatigue crack.

The procedures discussed above provide the data needed to calculate the internal stress intensity factors that affect the overall fatigue damage.

Now turning to environmental factors that affect fatigue damage, in general, the environment affects the fatigue damage characteristics over the entire crack growth regions. At or near the threshold region, the effect is more time dependent, while at higher growth rates it is more stress dependent. At higher stresses where plasticity would become important, the environment affects the behavior synergistically with the mechanical driving forces. These variations are reflected on a da/dN–$\Delta K_{appl}$ curve at different regions.

Corrosion-fatigue within an aqueous environment can be summarized into number of items. Corrosion pits can serve as crack nucleation sites during fatigue scenarios. Preferential electrochemical attack occurs at slip bands where there is slip localization. Preferential electrochemical attack can also occur at sites where oxide film has ruptured. Surface energy reduction due to chemical absorption can also increase crack growth rates. Diffusion of the damaging species through freshly created slip steps can also occur. Transportation of the nascent hydrogen by dislocations moving out of crack tip can further accelerate damage. Trapping and creating brittleness by hydrogen at grain boundaries and other traps ahead of the crack tip can also occur.

The rates of chemical attack and their influence on fatigue life are strongly influenced by the electrochemistry of the environment which can accentuate the mechanical damage process. The damage process may then fall into either anodic/cathodic dissolution or hydrogen embrittlement. This makes fatigue analysis that accounts for the environmental effects of corrosion difficult to understand and quantify for use in a life prediction model.

Figure 9A:
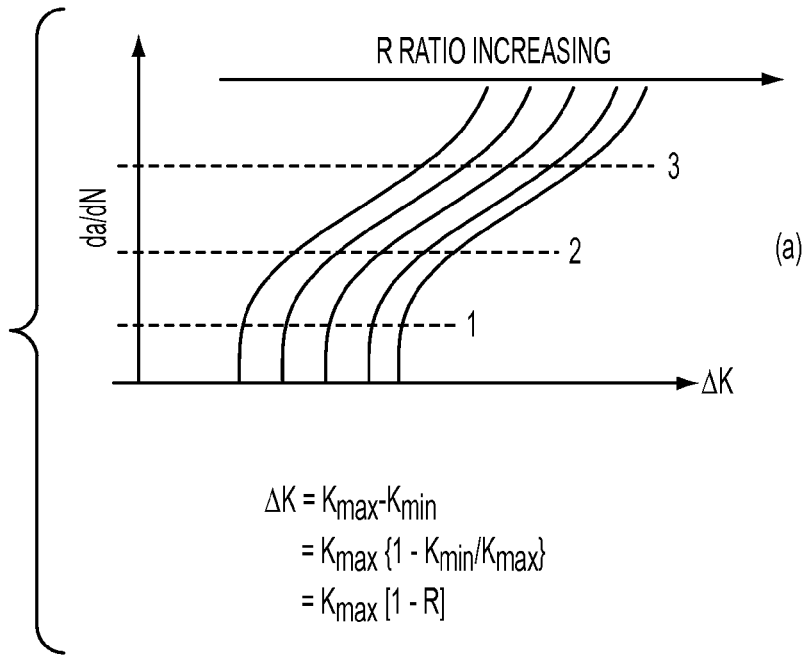
FIG. 9(a) is a schematic of fatigue crack grow data at various R ratios showing stress distribution near a blunt crack under tension loading.
Figure 9B:
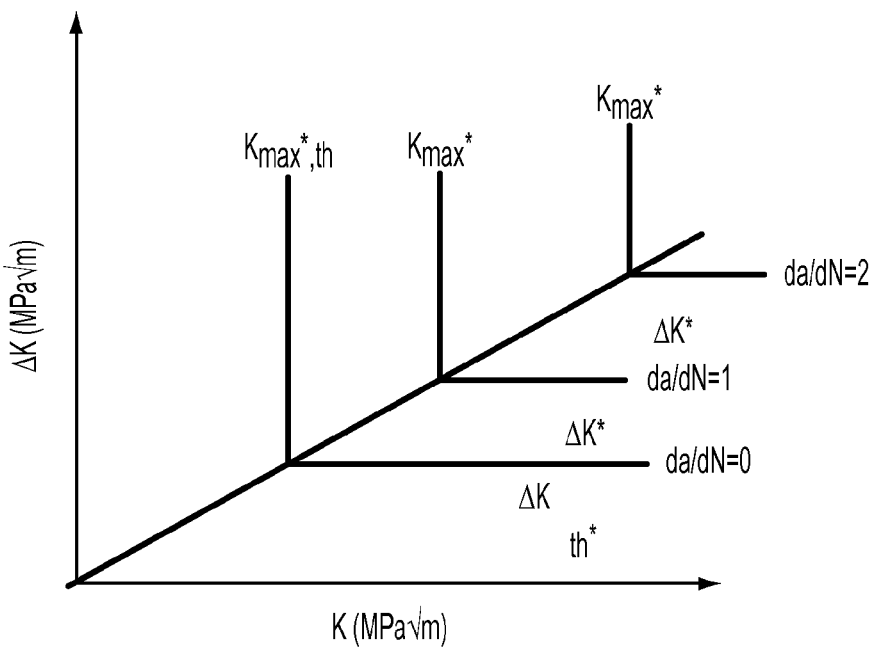
FIG. 9(b) is a graph showing two limiting values $\Delta K^*$ and $K^*_{max}$ for each crack growth rate in the unified fatigue damage approach.
Figure 9C:
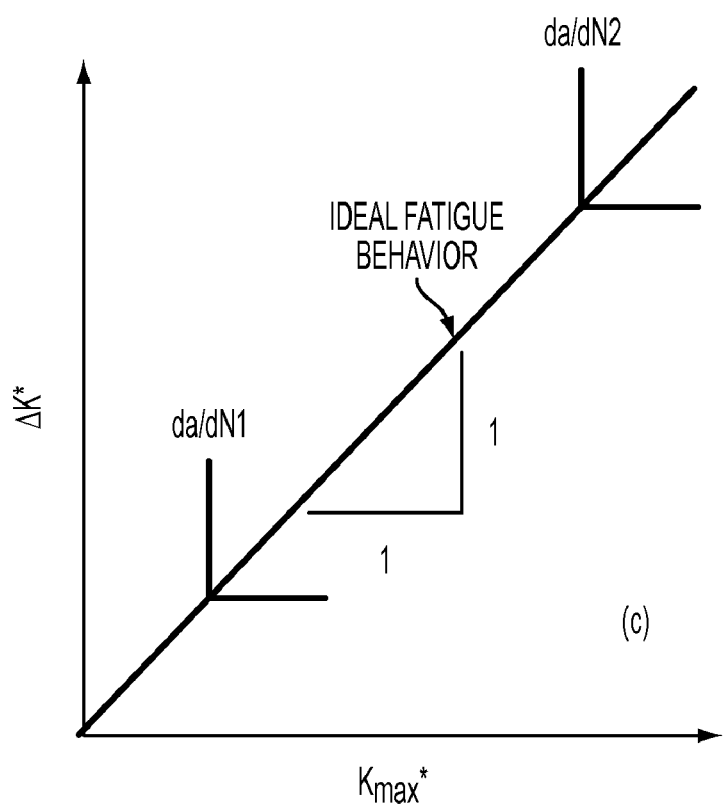
FIG. 9(c) is a graph showing the variations $\Delta K^*$ and $K^*_{max}$ with crack growth rates.
Figure 10:
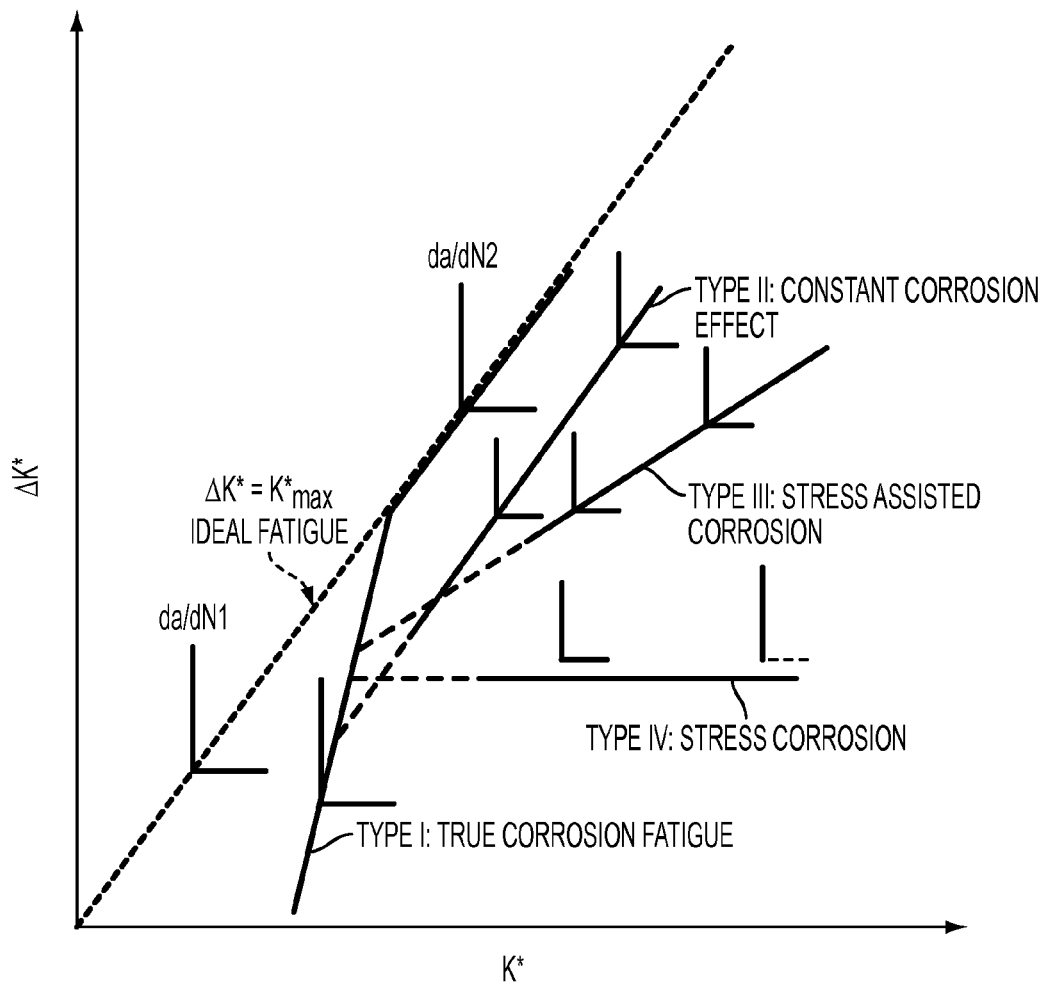
FIG. 10 is a graph showing the classification of environmental effects on fatigue crack growth rates into four types using the graphs shown in FIG. 9(c).

As a step towards analyzing the corrosion contribution to fatigue damage, the unified fatigue damage approach is used to map the overall behavior of a component. The environment typically provides a time-dependent damage and is generally characterized by $K_{max}$. As discussed above, FIGS. 3 and 4 show a plot for the 2024 data as $\Delta K_{appl}$–$K_{max,appl}$ near the threshold region, where (da/dN)~$10^{-10}$ m/cycle. One can represent such plots for any (da/dN) and obtain a series of $\Delta K_{appl}$–$K_{max}$ behaviors as a function of crack growth rate. From this series a trajectory map can be made to include the variation of the two limiting values as a function of crack growth rate. FIG. 9 shows a schematic of typical experimental fatigue crack growth rate curves with $\Delta K_{appl}$ at many R-ratios. Taking constant sections of (da/dN) at various selected growth rates and plotting them as a series of $\Delta K_{appl}$–$K_{max,appl}$ curves, as shown in FIGS. 9(a)-9(c), and joining the corners of the $\Delta K_{appl}$–$K_{max,appl}$ plots gives a component material's crack growth trajectory path. This represents the component material's resistance to crack growth in a given environment. Using this procedure, the dynamics of material crack growth resistance can be represented in the unified fatigue damage approach in terms of the crack tip driving force parameters $\Delta K_{appl}$ and $K_{max,appl}$ on to a single plot. Using this method, one can determine the role of a given environment and material in relation to an inert background, which is represented by a 45° line. It has been observed that in most of the component materials the environmental behaviors fall into four types of corrosion mechanisms when the experimental results are plotted as shown in FIG. 9(a)-9(c). This is shown in FIG. 10. In FIG. 10 the 'ideal fatigue' is a 45° line where $\Delta K^*_{appl}$ and $K^*_{max,appl}$ represents fatigue damage that is controlled by purely cyclic damage. Absence of any R-ratio effect in da/dN-$\Delta K_{appl}$ plot is a characteristic of this damage process. This is observed in many alloys tested in a very good vacuum and also in several small grain size (<10 μm) alloys tested in lab air with some humidity. Deviations from this 'ideal fatigue' behavior are indicative of environmental contributions to damage.

Still referring to FIG. 10, type-I gives true corrosion fatigue where at low $K_{max,appl}$ time-dependent effects of the environment dominate, eventually merging with the 'ideal' behavior when the crack growth kinetics are greater than the corrosion kinetics. In Type I, the environmental contribution decreases with an increase in crack growth rate indicating that the mechanism is time related and hence a frequency-dependent process. In Type-II, there is a constant corrosion effect that persists for all crack growth rates, indicating that corrosion effect is constant and does not vary significantly with crack growth rate, stress or $K_{max,appl}$. In Type-III, the deviation from a 45° line increases with $K_{max,appl}$ suggesting stress assisted corrosion phenomena. Here corrosion effects increase with $K_{max,appl}$ and $\Delta K_{appl}$. Thus, enhanced fatigue and corrosion-fatigue contribute to the increased crack growth rates. Finally, in Type-IV a stress corrosion process is shown where there is a small background effect from $\Delta K_{appl}$. The result is an increased crack growth rate that is manifested only by increasing $K_{max,appl}$ through corrosion while fatigue ($\Delta K_{appl}$) keeps the crack tip sharp. FIG. 10 is able to illustrate experimental trends using a map in which different types of corrosion-fatigue behavior are represented.

Figure 11:
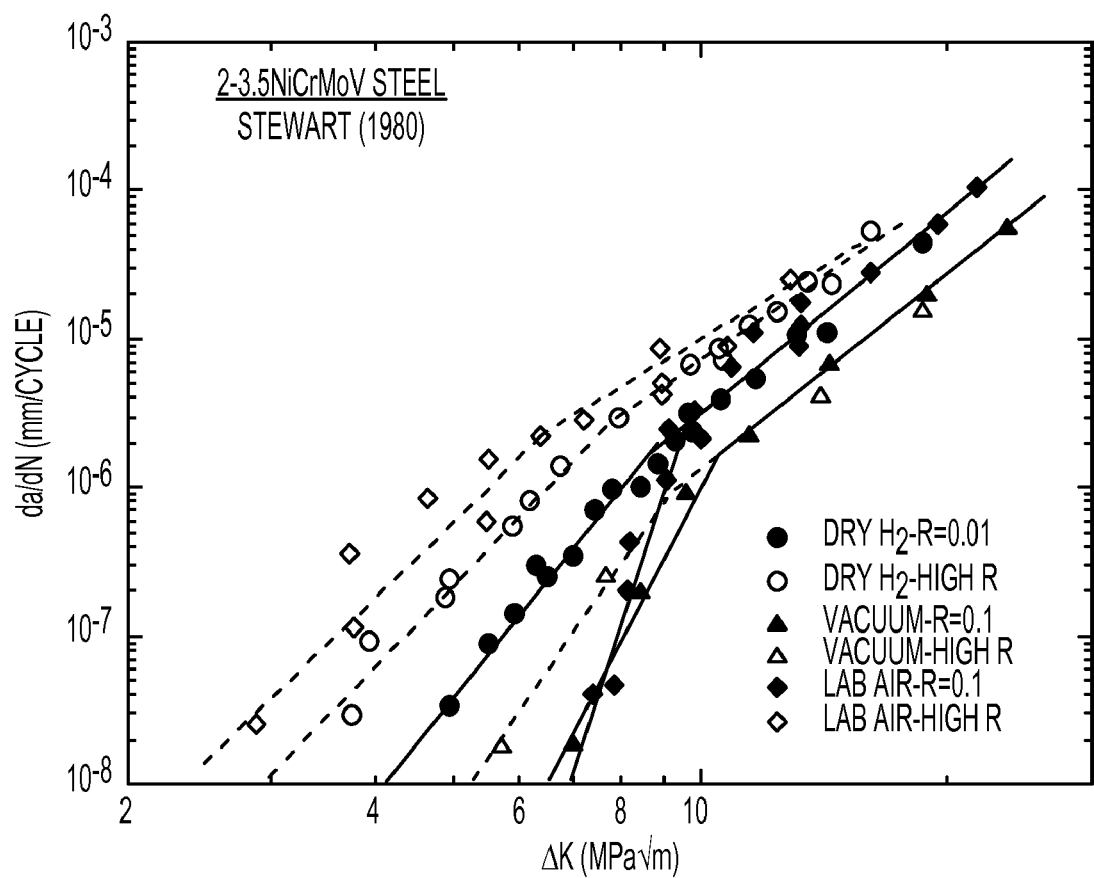
FIG. 11 is graph showing the fatigue crack growth rate results in three different environments on low alloy NiCrMo steel.
Figure 12:
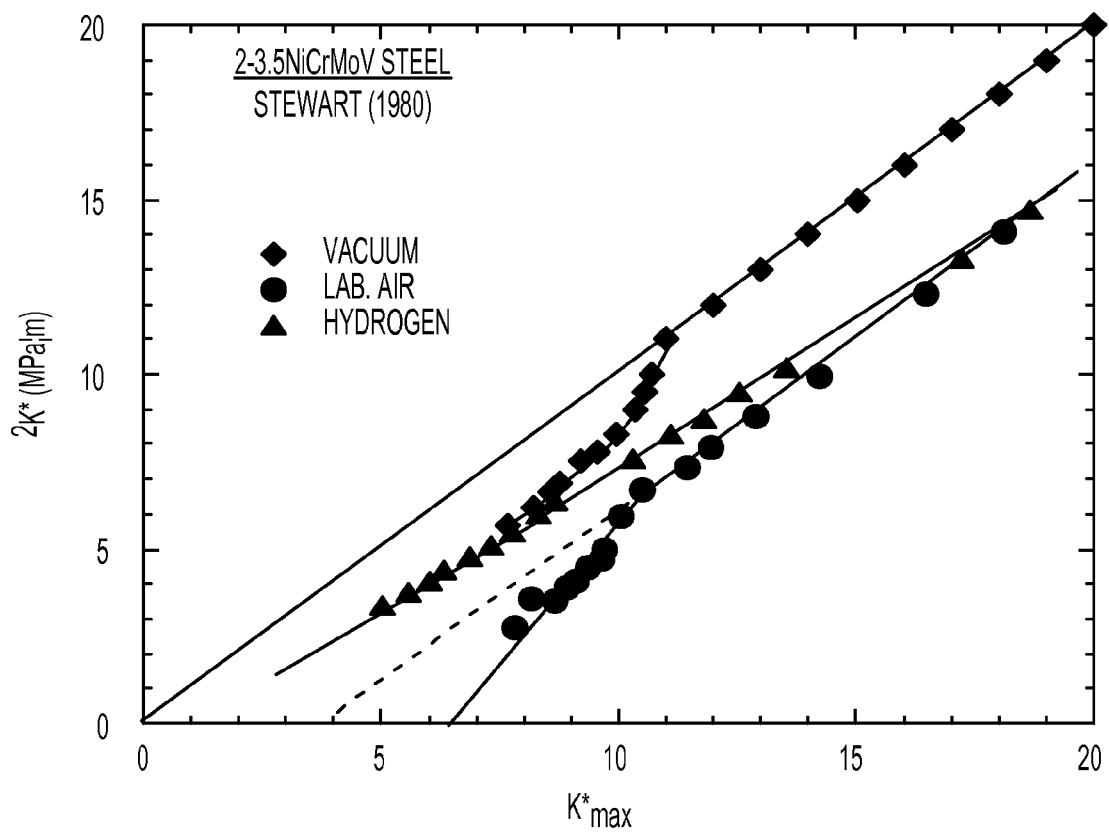
FIG. 12 is graph showing the classification of the behavior shown in FIG. 11.
Figure 13:
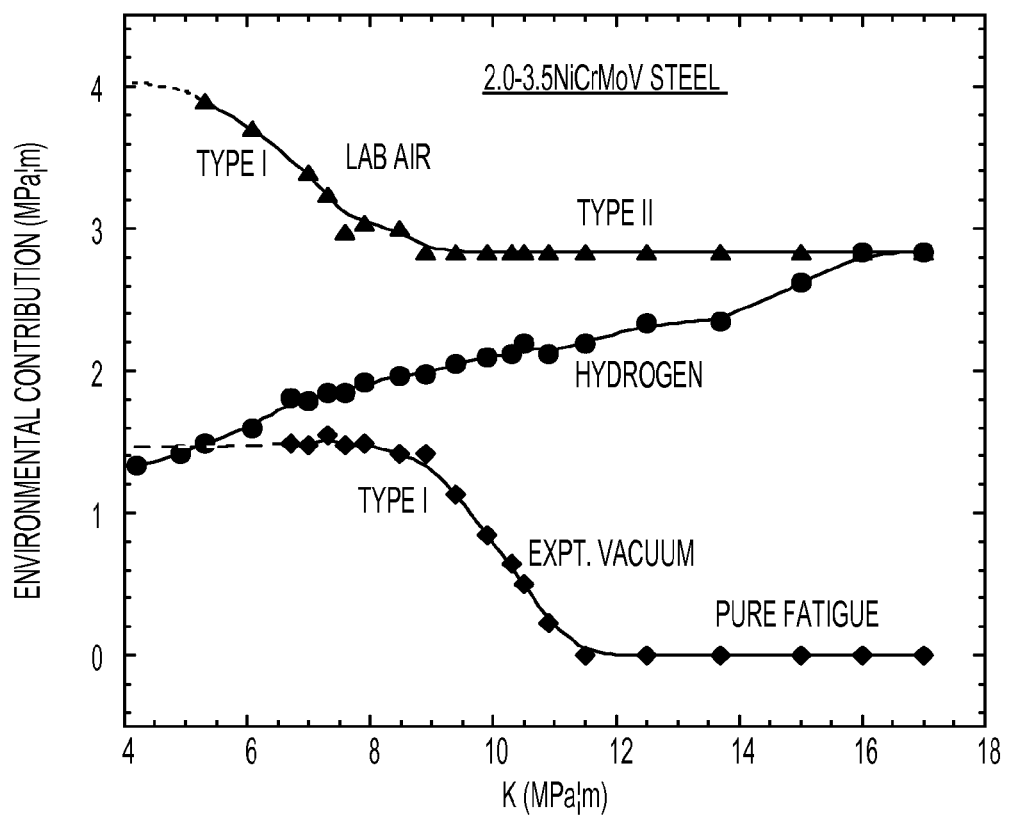
FIG. 13 is graph quantifying the environmental contribution using classification behavior shown in FIG. 12 as a function of $K^*_{max}$.

Examples of the description shown in FIG. 10 are shown in FIGS. 11-13, which show three basic types of mechanisms in steel. FIG. 11 shows the high and low R-ratio crack growth rate curves in a vacuum, lab air and dry hydrogen for NiCrMo-steels. FIG. 12 shows the $\Delta K^*_{appl}$ and $K^*_{max,appl}$ plot showing the three types of corrosion assisted fatigue behavior of Types-I, II and III. From FIG. 12 the environmental contribution to $K_{max}$ can be extracted and is shown in FIG. 13. It can be seen that lab air and vacuum are similar in behavior, but displaced in magnitude; the vacuum (~$10^{-6}$ torr) is poor. Initially, the environmental contribution was high and eventually it decays into a constant value of about 2.8 MPa√m when $K_{max}$ reaches 8 MPa√m (for air) and zero when $K_{max}$ reaches 10 MPa√m (for vacuum). The environmental contribution is measured as an excess (negative) mechanical force in relation to the ideal case. Thus, it can be considered as a mechanical equivalent of the chemical driving force aiding the crack growth and causing the deviation from the ideal inert behavior (the 45° line in FIG. 13). In the vacuum case, the environmental contribution goes to zero relative to air. In contrast, the environmental contribution continuously increases with $K_{max}$ for dry hydrogen, showing that the embrittlement process is a stress driven process such as in stress-corrosion. This is corrosion fatigue of Type III.

Figure 14:
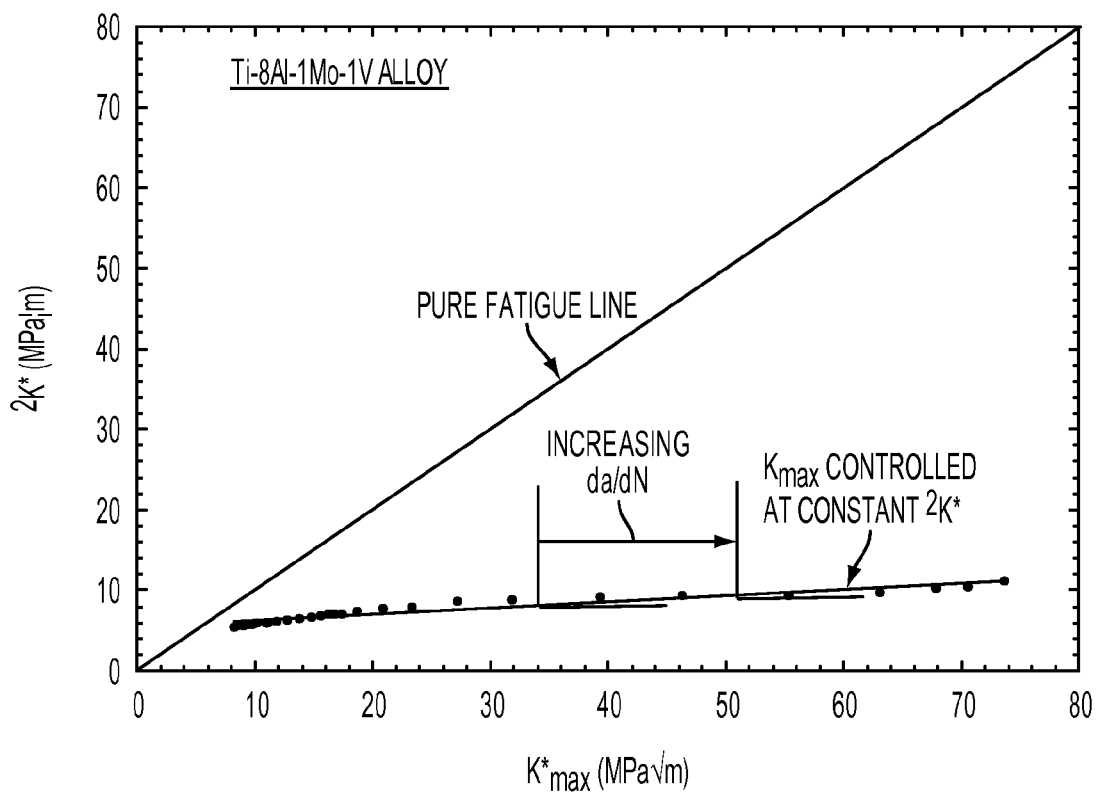
FIG. 14 is graph of Type IV behavior observed in Ti-alloy in a NaCl environment.
Figure 15:
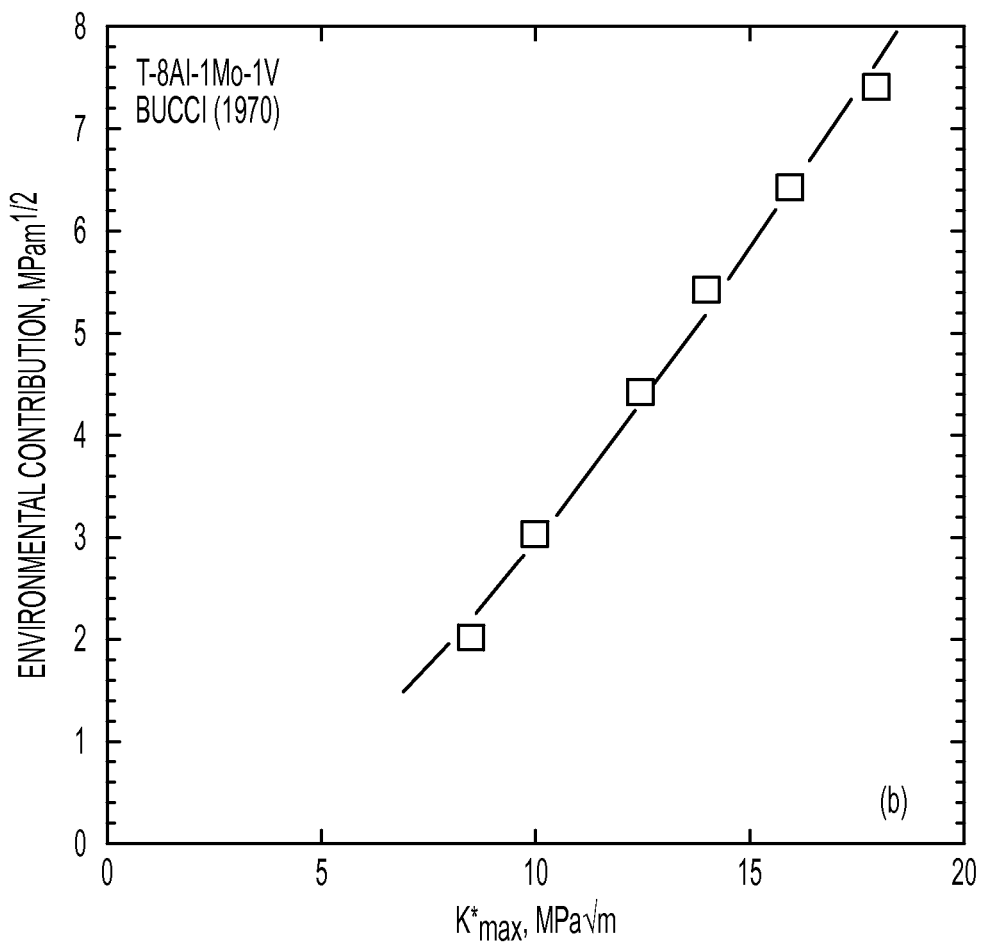
FIG. 15 shows the magnitude of environmental contribution to $K^*_{max}$.

Type IV behavior is shown in FIG. 14 for a Ti-AlMoV alloy in NaCl. Here the environmental contribution increases with stress, $K^*_{max}$. The overall contribution is mostly stress driven rather than reaction time controlled. The result is that the curve shows a maximum deviation from the ideal behavior (the 45° line). The magnitude of the environmental contribution can be extracted from FIG. 14 and is shown in FIG. 15. Here the environmental contribution continuously increases with $K^*_{max}$ with no change in the mechanism. This is purely an environmental effect. Fatigue only maintains the crack tip sharp, while the environment contributes to crack growth damage.

The relative contributions of environmental effects to the driving force $K_{max}$ can be quantified. At near threshold crack growth rates, fatigue contribution (from $\Delta K_{appl}^*$ and $K^*_{max}$) is coupled with environmental contributions to $K_{max}$. Here, the environmental effects come from the chemical potential gradient and its kinetics. While the cycle dependent effects are coming from (da/dN), the time-dependent effects from the environment constitute (da/dt). The overall (da/dN) has two effects embedded in it: one cycle dependent and one time dependent. Separating these two contributions becomes important when analyzing the effects of fatigue crack growth using the kinetics of corrosion. At higher growth rates, an additional contribution would come from the overload fracture.

In summary, the unified fatigue damage model is a two parametric problem described in terms of $\Delta K_{appl}^*$ and $K^*_{max,appl}$ that depends on the environment, loads and alloy microstructure. For a crack to grow both threshold values need to be simultaneously satisfied. Long crack growth behavior is the basic material property and any deviations from it are due to internal stresses. Without invoking crack closure, the fatigue life prediction can be made using $\Delta K_{appl}$, $K_{max,appl}$ and $K_{int}$ for real systems with service load environments. Environmental effects can be described with the $\Delta K_{appl}$ and $K_{max,appl}$ approach and can be represented in terms of a trajectory map that describes the regions of mechanisms operating for a given alloy. Thus, the unified fatigue damage approach provides a method for predicting the useful life of components in a reliable manner.

Figure 16:
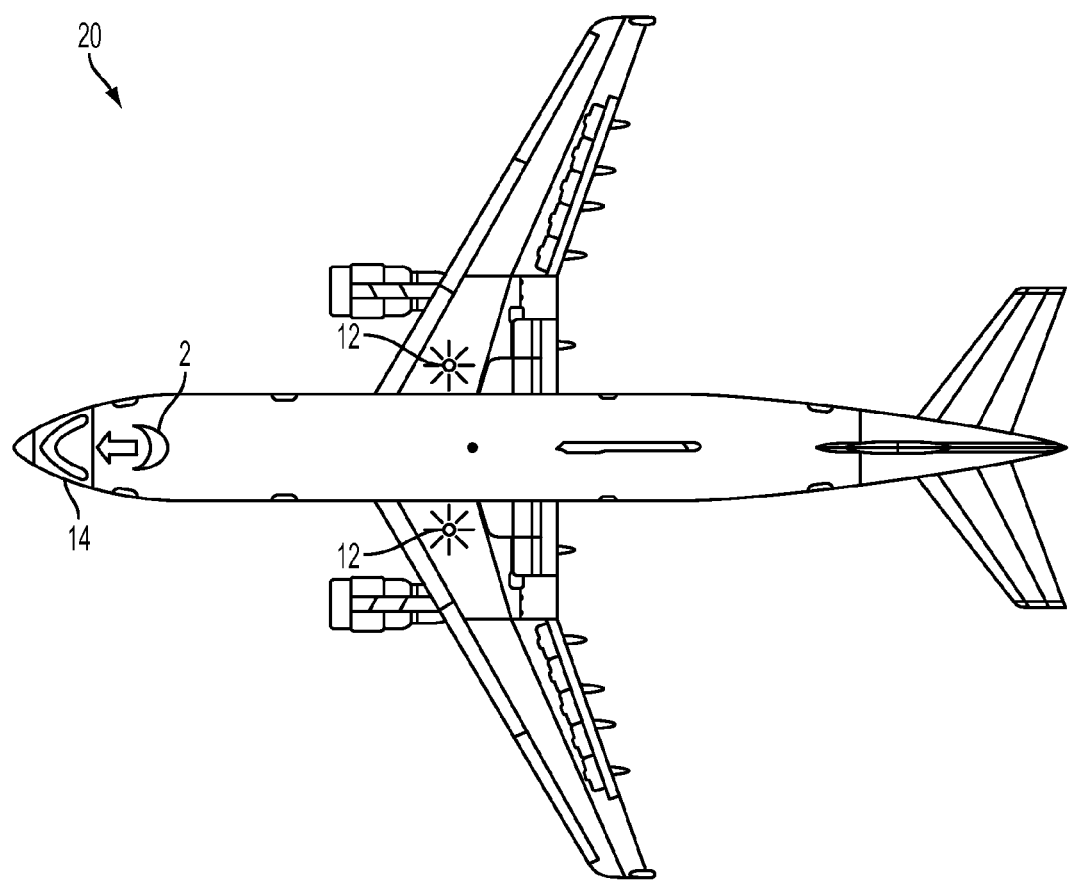
FIG. 16 shows an airplane equipped with a system for component damage prediction in accordance with an embodiment of the present invention.
Figure 17:
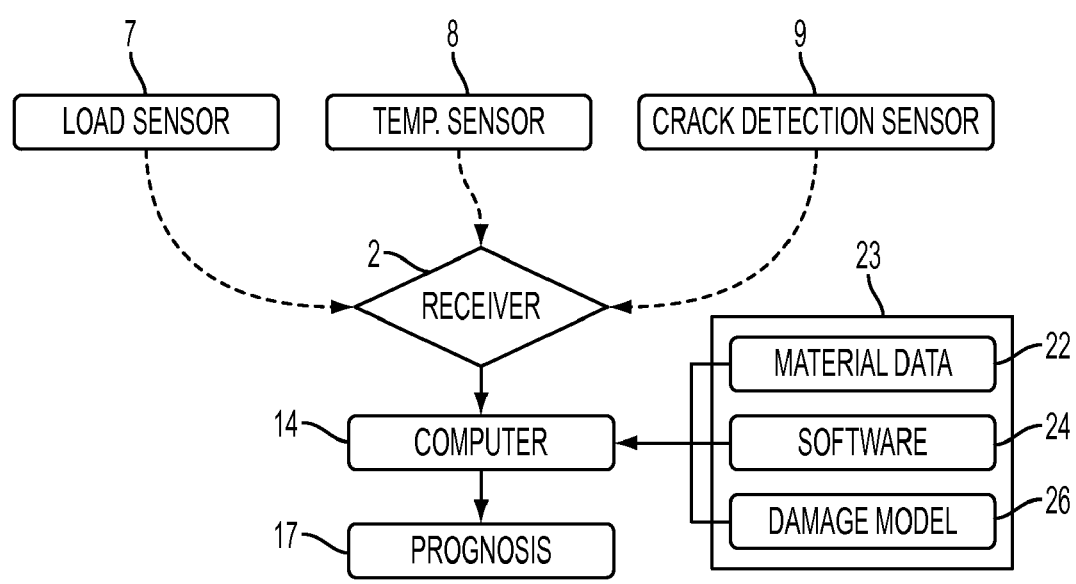
FIG. 17 is diagram of the system for component damage prediction in accordance with the embodiment of the present invention shown in FIG. 16.

FIGS. 16 and 17 show a system for predicting component damage. Failures in component structural life prediction and damage prognosis are associated with a lack of real-time input data actually experienced by the structures during their life cycle.

FIG. 16 shows an aircraft 20 that has attached to it and/or embedded within it sensors 12. Critical locations on the aircraft 20 may be selected using finite element analysis (FEA). Such analysis will permit determination of the locations that are prone to fatigue cracks, where the stresses, temperature and humidity/corrosion are crucial. Those places on the aircraft 20 which are prone to cracking are typically selected for placement of the sensors 12. The sensors 12 may then transmit data to a receiver 2 that can be located at the front of the aircraft 20 within the cabin, or alternatively may be located elsewhere on the aircraft 20. The receiver 2 may then transmit the received data to a computer 14 that is programmed to take the received data and analyze it.

FIG. 17 shows a system diagram of the embodiment of FIG. 16. Sensors 12 may be a load sensor 7, temperature sensor 8, or crack detection sensor 9. It should be understood that other physical variables could be tested in order to determine environmental and physical characteristics of the components being tested on the aircraft 20 (e.g. loading condition, pressure, humidity, etc.). The sensors 12 may be integrated with real-time tracking capacity of mechanical, thermal and chemical parameters and can be used together in making the prediction. The real-time input data may be transmitted from the sensors 7,8 and 9 to the receiver 2 and then be networked to a computer 14 that can then analyze the data and provide a prognosis 17 related to any potentially dangerous situations.

Computer 14 may be a processor connected to a memory storage device, such as database 23 shown in FIG. 17. Computer 14 may also be a networked computer or plurality of computers connected to a network, such as WAN or LAN, which is able to process the received empirical data and correlate with stored material data 22 related to the components of the aircraft 20, so that a prognosis 17 can be made. The program for making prognosis 17 can be stored on software 24 and can be used by the unified fatigue damage model 26 along with the empirical data and the material date 22 in order to generate prognosis 17.

In general, the actual loading conditions to which the structure would be subjected during service are not fully known. Usually a selected snapshot of mechanical loading is used in fatigue life predictions assuming some hypothetical thermal and environmental conditions. In such predictions, though practically experienced loading conditions are used in the calculations, other environmental conditions and related parameters (e.g. temperature of the system in that loading condition, pressure, humidity etc.) are assumed to be equal to the typical average values, which are bound to result in less than accurate predictions of the fatigue life. Therefore, current practice relies on utilization of periodic nondestructive evaluations (NDE) in order to infer information on the current state of structural integrity. The periodic inspection intervals are estimated based on fatigue damage or crack propagation models and simplified input data regarding service loading conditions. As such, the calculated inspection intervals are treated as a starting point to set a real inspection schedule. Too frequent inspections can result in excessive cost and infrequent inspections may increase the safety risk.

Therefore, the use of sensors 12 to provide integrated real-time tracking capability of mechanical, thermal and chemical loadings is an application of a unified fatigue model that can provide reliable life and damage prognoses for such structures, as well as for vehicles such as aircraft, aerospace vehicles, and ground vehicles, power-plants, bridges, ships and off-shore oil drilling platforms.

Figure 18:
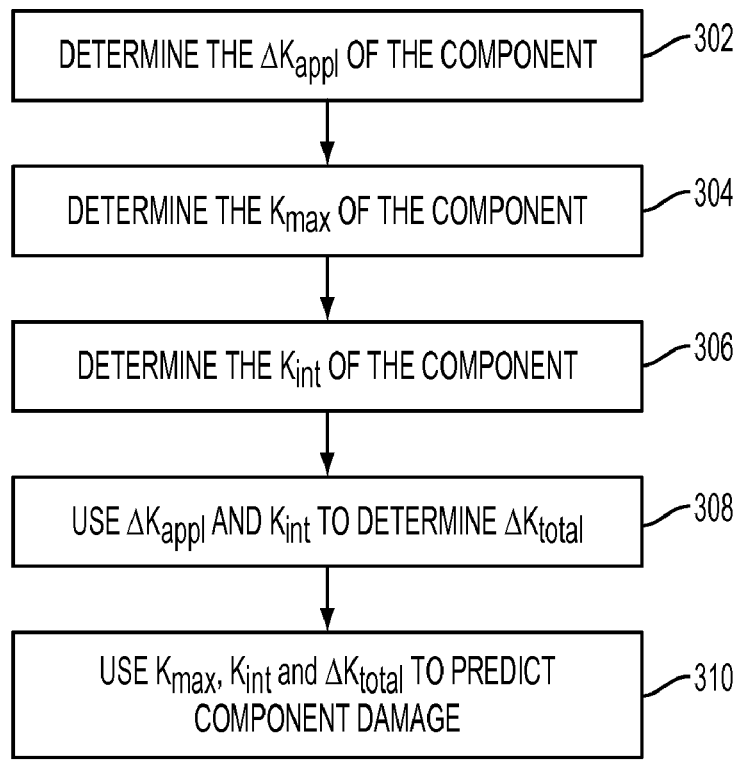
FIG. 18 is a flow chart of a method for determining component damage in accordance with an embodiment of the present invention.

FIG. 18 provides a general overview of the method used in applying the unified fatigue damage model, which has been discussed in detail above. Generally, the method disclosed in FIG. 18 is applicable to the system shown in FIGS. 16-17. Further details regarding the derivation of the values $\Delta K_{appl}$, $K_{max,appl}$, $\Delta K_{total}$, $K_{max,total}$ and $K_{int}$ may be found in the discussion above.

At step 302 the $\Delta K_{appl}$ of the component is determined. This value can be determined based upon known empirical data or through the conduction of experiments on various materials that are used to make the components that are to be tested. This value can be stored in a database such as database 23. In the system shown in FIGS. 16-17, this material information would have been determined at some point prior to an actual flight or prior to the analysis that is performed by computer 14 based upon data received from sensors 12. It is also possible to utilize sensors 12 in order to further determine the values used in the unified fatigue model.

At step 304, the value of $K_{max}$ for a component is also determined in much the same manner that $\Delta K_{appl}$ was determined. At step 306, $K_{int}$ is determined and this may be accomplished through various non-invasive experimental techniques, such as X-ray diffraction. The value for $K_{int}$ may also be determined in a real-time manner using sensors 12. As discussed above, the environmental factors that may also be determined by sensors 12 can be factored into the value for $\Delta K_{int}$ and can ultimately play a role in the implementation of the unified fatigue damage model.

At step 308, $\Delta K_{appl}$ and $K_{int}$ are used to together in order to determine a value of $\Delta K_{total}$. At step 310, these obtained values are used together in order to predict damage to components. Included in the prediction is the failure state of the component. As an advantage for the unified fatigue damage model, predictions can begin at 0.1 mm of resolution versus 1.2 mm of resolution for typical inspection methods.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed as new and desired to be protected by Letters Patent of the United States is:

1. A method for component damage prediction in real world service environments comprising:
   determining $\Delta K_{appl}$ and $K_{max,appl}$ of the component from service life load data, said service life having varying maximum loads and environmental conditions;
   experimentally determining $K_{int}$ and $\Delta K_{int}$ of the component by measuring crack tip displacements as a function of distance from crack tip;
   determining $\Delta K_{total}$ as a sum of the $\Delta K_{appl}$ and the $\Delta K_{int}$ of the component; and
   predicting crack growth rate da/dN according to $$\frac{da}{dN} = C\{\Delta K_{total}^{1-p} K_{max,total}^{P}\}^{\gamma},$$

wherein p is a driving force constant, $\gamma$ a fatigue growth equation exponent, and p and $\gamma$ are empirically determined from fitting a Coffin-Manson curve to strain-controlled fatigue test data of the component, C is a fatigue crack growth constant computed from the Coffin-Manson curve and the strain-controlled fatigue test data, $\Delta K_{appl}$ is applied stress intensity range, $K_{max,appl}$ is a maximum applied stress intensity factor, $K_{int}$ and $\Delta K_{int}$ are internal stress intensity factors due to internal stresses, and $K_{max,total}$ is a total maximum stress intensity factor calculated as a sum of $K_{int}$ and $K_{max,appl}$.

2. The method of claim 1, wherein said measuring crack tip displacements is accomplished using X-Ray diffraction.

3. The method of claim 1, wherein the value of p is determined from plastic and elastic slopes obtained from the strain controlled fatigue test data.

4. The method of claim 3, wherein the value of $\gamma$ is determined from cyclic hardening rates obtained from the strain controlled fatigue test data.

5. The method of claim 1, wherein $\Delta K_{int}$ encompasses effects of residual stresses, corrosion, temperature, oxidation, and creep.

6. The method of claim 1, wherein an internal stress, $\sigma_{int}$, of the component is calculated prior to determining $K_{int}$.

7. The method of claim 6, wherein the internal stress, $\sigma_{int}$, is calculated using an Elastic equation or a Rice equation.

8. The method according to claim 1, wherein said determining $K_{int}$ includes a non-destructive test.

9. The method of claim 1, wherein said determining the $K_{int}$ of the component includes synchrotron X-Ray diffraction.

10. The method according to claim 1, wherein the component comprises metal, metal composites, ceramic composites, or polymer composites.

11. The method according to claim 1, wherein the component comprises at least one of aluminum, titanium, iron, copper, and magnesium.

12. The method according to claim 1, wherein the component is a high temperature material in an engine.

13. A system for component crack growth prediction comprising:
   a sensor enabled to determine empirical data related to the component;
   a receiver operably connected to a computer;
   a database operably connected to the computer, wherein material data related to the component is stored;
   wherein the computer is programmed to receive and use the empirical data and the material data related to the component in order to
   predict crack growth rate da/dN according to $$\frac{da}{dN} = C\{\Delta K_{total}^{1-p} K_{max,total}^{P}\}^{\gamma},$$

wherein p is a driving force constant, $\gamma$ is a fatigue growth equation exponent, and p and $\gamma$ are empirically determined from fitting a Coffin-Manson curve to strain-controlled fatigue test data of the component,
wherein C is a fatigue crack growth constant computed from the Coffin-Manson curve and the strain-controlled fatigue test data, $\Delta K_{total}$ is a sum of $\Delta K_{appl}$ and $\Delta K_{int}$ of the component, $\Delta K_{appl}$ is applied stress intensity range, $K_{max,appl}$ is a maximum applied stress intensity factor, and $\Delta K_{appl}$ and $K_{max,appl}$ of the component are determined based on service life load data, said service life having varying maximum loads and environmental conditions.

14. The system of claim 13, wherein the sensor is selected from the group consisting of a load sensor, a temperature sensor and a crack detection sensor.

15. The system of claim 13, wherein the sensor and the receiver are located on an aircraft.

* * * * *